US012708451B2

(12) United States Patent
Fanson et al.

(10) Patent No.: US 12,708,451 B2
(45) Date of Patent: Aug. 18, 2026

(54) OPERATING ROOM REMOTE MONITORING

(71) Applicant: INTELLIJOINT SURGICAL INC., Kitchener (CA)

(72) Inventors: Richard Tyler Fanson, Stoney Creek (CA); Andre Novomir Hladio, Waterloo (CA); Samantha McCabe, Kitchener (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 8 days.

(21) Appl. No.: 18/645,028

(22) Filed: Apr. 24, 2024

(65) Prior Publication Data

US 2024/0341862 A1 Oct. 17, 2024

Related U.S. Application Data

(63) Continuation of application No. 16/965,971, filed as application No. PCT/CA2019/050128 on Feb. 1, 2019, now abandoned.

(Continued)

(51) Int. Cl.

*A61B 34/20* (2016.01)
*A61B 34/00* (2016.01)

(Continued)

(52) U.S. Cl.

CPC .............. *A61B 34/20* (2016.02); *A61B 34/10* (2016.02); *A61B 34/25* (2016.02); *A61B 34/35* (2016.02);

(Continued)

(58) Field of Classification Search

None

See application file for complete search history.

(56) References Cited

U.S. PATENT DOCUMENTS 7,317,955 B2 1/2008 McGreevy
8,321,797 B2 11/2012 Perkins (Continued)

FOREIGN PATENT DOCUMENTS

CA 2840397 A1 4/2013
WO 2017147596 A1 8/2017

OTHER PUBLICATIONS

Surgical Theater; VR Medical Visualization Platform; Article; 2019; 8 Pages.

(Continued)

*Primary Examiner* — Yi-Shan Yang

(57) ABSTRACT

OR computing system monitoring is described including self-monitoring and monitoring, with or without intervention, via a monitoring computing system. For a patient procedure in an OR, positions of one or more objects are tracked using sensors. Intra-operative data including pose information is communicated (e.g. in real time) to a monitoring computing system to present the intra-operative data including object positions in a GUI. Pose information may be sensor data with which to calculate a pose of an object or pre-calculated pose data. Intra-operative data may be a workflow state of the procedure to display workflow UI screens. A virtual view of the OR may be presented from pose information and geometric data for OR equipment. Working volumes of OR equipment including collision warning may be presented. OR equipment may include a localizer and/or a robot. Self-monitoring may evaluate progress in a procedure and trigger a request (e.g. to monitor).

20 Claims, 6 Drawing Sheets

Related U.S. Application Data

(60) Provisional application No. 62/625,511, filed on Feb. 2, 2018.

(51) Int. Cl.
*A61B 34/10* (2016.01)
*A61B 34/35* (2016.01)
*A61B 34/37* (2016.01)
*G16H 20/40* (2018.01)
*G16H 40/67* (2018.01)

(52) U.S. Cl.
CPC .............. *A61B 34/37* (2016.02); *A61B 34/70* (2016.02); *G16H 20/40* (2018.01); *G16H 40/67* (2018.01); *A61B 2034/105* (2016.02); *A61B 2034/2055* (2016.02); *A61B 2034/2059* (2016.02); *A61B 2034/2072* (2016.02); *A61B 2505/05* (2013.01)

(56) References Cited

U.S. PATENT DOCUMENTS 9,192,445 B2 11/2015 Kang
9,452,023 B2 9/2016 Boillot et al.
9,654,739 B1 5/2017 Mitchell et al.
9,788,907 B1 10/2017 Alvi et al.
11,317,979 B2 5/2022 Itkowitz et al.
2004/0068187 A1 4/2004 Krause et al.
2006/0258938 A1* 11/2006 Hoffman .................. A61B 5/06 600/424
2013/0211421 A1 8/2013 Abovitz et al.
2014/0107471 A1* 4/2014 Haider ................. A61B 5/1076 606/82
2016/0314717 A1* 10/2016 Grubbs ................ G09B 23/306
2017/0367771 A1 12/2017 Tako et al.
2021/0353311 A1* 11/2021 Lavallee ................ A61B 34/20

OTHER PUBLICATIONS

Hu et al.; Advanced Visualization Platform for Surgical Operating Room Coordination Distributed Video Board System; Article; Jun. 2006; 7 Pages; vol. 13 No. 2; Sage Publications.

Agarwal et al.; The Roboconsultant Telementoring and Remote Presence in the Operating Room During Minimally Invasive Urologic; Article; 5 pp. 970-974; 2007; Elsevier Inc.

International Search Report Dated Apr. 18, 2019 For Corresponding International PCT Patent Application No. PCT/CA2019/050128; 3 Pages.

Written Opinion Dated Apr. 18, 2019 For Corresponding International PCT Patent Application No. PCT/CA2019/050128; 5 Pages.

* cited by examiner

OPERATING ROOM REMOTE MONITORING

CROSS-REFERENCE

This application is a continuation of Ser. No. 16/965,971, entitled "Operating Room Remote Monitoring", having a 371(c) date of Jul. 29, 2020, the entire contents of which are incorporated herein by reference. The '971 application is a 371 of PCT/CA2019/050128 filed Feb. 1, 2019, which claims the benefit of 62/625,511 filed Feb. 2, 2018.

FIELD

This disclosure relates to monitoring operating rooms remotely using computing systems and more particularly to monitoring surgical navigation and other operating room (OR) computing systems where monitoring may include observing and/or intervening in a computer-assisted procedure performed by the OR computing system.

BACKGROUND

Surgical navigation and other OR computing systems are prevalent in operating rooms to assist with certain types of procedures. Some such systems perform localization, tracking a pose of objects used during the procedure while others such as those using robots also manipulate the pose of objects during the procedure. OR computing systems and the related computer-assisted procedures have high accuracy tolerances. These tolerances may drive desired positive outcomes of the respective procedures. A surgeon must not only trust the OR computing system but must achieve accurate information and results from the OR computing system. Ending a procedure due to issues with an OR computing system may be intolerable. Prolonging a procedure due to issues with an OR computing system may be undesirable. Furthermore minimizing a number of attending personnel within an OR may be indicated to address infection risk, cost and/or privacy concerns.

SUMMARY

OR computing system monitoring is described including self-monitoring and monitoring, with or without intervention, via a monitoring computing system. For a patient procedure in an OR, positions of one or more objects are tracked using sensors. Intra-operative data including pose information is communicated (e.g. in real time) to a monitoring computing system to present the intra-operative data including object positions in a GUI. Pose information may be sensor data with which to calculate a pose of an object or pre-calculated pose data. Intra-operative data may be a workflow state of the procedure to display workflow UI screens. A virtual view of the OR may be presented from pose information and geometric data for OR equipment. Working volumes of OR equipment including collision warning may be presented. OR equipment may include a localizer and/or a robot. Self-monitoring may evaluate progress in a procedure and trigger a request (e.g. to monitor).

In one aspect, there is provided an OR computing system comprising: at least one processing unit; a data store comprising a memory or other storage; and a communication system coupled to the at least one processing unit to couple the OR computing system to a communication network; wherein the data store and communication system are coupled to the at least one processing unit. The data store stores instructions which, when executed by the at least one processing unit, configure the OR computing system to: perform a computer-assisted procedure relative to a patient, tracking respective positions of one or more objects during the computer-assisted procedure in an operating room in which sensor data, representing the respective positions of the one or more objects within the operating room, is received from sensors associated with the one or more objects; and during the computer-assisted procedure (e.g. in real time), communicate intra-operative data generated during the procedure including pose information to a monitoring computing system for monitoring the operating room, the monitoring computing system configured to receive and present the intra-operative data in a GUI comprising the respective positions of one or more of the objects. The pose information comprises one or both of: sensor data with which to calculate a pose of an object; and pose data representing the pose of the object as calculated by the OR computing device using the sensor data.

In one aspect, there is provided a monitoring computing system to monitor a remotely located operating room containing an OR computing system. The OR computing system is configured to perform a computer-assisted procedure relative to a patient, tracking respective positions of one or more objects during the computer-assisted procedure in which sensor data, representing the respective positions of the one or more objects, is received from sensors coupled to the one or more objects. The monitoring computing system comprises: at least one processing unit; a data store comprising a memory or other storage; a display device; and a communication system to communicate with the OR computing system via a network. Each of the data store, display device and communication system are coupled to the at least one processing unit. The data store stores instructions which, when executed by the at least one processing unit, configure the monitoring computing system to: obtain geometrical data representing the one or more objects; receive (e.g. during a procedure in real time) from the OR computing system, relative to the computer-assisted procedure, intra-operative data including pose information; and present in a GUI, by displaying via the display device, at least some of the intra-operative data including the respective positions of the one or more objects using the pose information and the geometrical data. The pose information comprises one or both of sensor data with which to calculate a pose of an object and pose data representing the pose of the object as calculated by the OR computing system using the sensor data.

In one aspect, there is provided an OR computing system comprising: at least one processing unit; a data store comprising a memory or other storage; and a communication system to communicate with the OR computing system via a network. Each of the data store, display device and communication system are coupled to the at least one processing unit. The data store stores instructions which, when executed by the at least one processing unit, configure the OR computing system to: perform a computer-assisted procedure, tracking respective positions of one or more objects during the computer-assisted procedure in an operating room, generating pose data representing the respective positions of the one or more objects in a reference space within the operating room; store log data with which to monitor a progress of the computer-assisted procedure; monitor the progress of the computer-assisted procedure using the log data; determine a measure of progress responsive to the monitoring; and responsive to the measure of progress, communicate a message identifying the measure of progress (and including at least some of the log data) to a remotely located monitoring computing system to monitor the OR computing system.

In one aspect, there is provided a method comprising: performing a computer-assisted procedure by an OR computing system relative to a patient, tracking respective positions of one or more objects during the computer-assisted procedure in an operating room in which sensor data, representing the respective positions of the one or more objects within the operating room, is received by the OR computing system from sensors associated with the one or more objects; and during the computer-assisted procedure (e.g. in real time), communicating intra-operative data generated during the procedure including pose information to a monitoring computing system for monitoring the operating room, the monitoring computing system configured to receive and present the intra-operative data in a GUI comprising the respective positions of one or more of the objects. The pose information comprises one or both of: sensor data with which to calculate a pose of an object; and pose data representing the pose of the object as calculated by the OR computing device using the sensor data.

In one aspect, there is provided a method to monitor a remotely located operating room containing an OR computing system configured to perform a computer-assisted procedure relative to a patient, tracking respective positions of one or more objects during the computer-assisted procedure in which sensor data, representing the respective positions of the one or more objects, is received from sensors coupled to the one or more objects. The method comprises: obtaining geometrical data representing the one or more objects; receiving (e.g. during a procedure in real time) from the OR computing system, relative to the computer-assisted procedure, intra-operative data including pose information; and presenting in a GUI, by displaying via a display device, at least some of the intra-operative data including the respective positions of the one or more objects using the pose information and the geometrical data. The pose information comprises one or both of sensor data with which to calculate a pose of an object and pose data representing the pose of the object as calculated by the OR computing system using the sensor data.

In one aspect, there is provided a method comprising: performing a computer-assisted procedure by an OR computing system, tracking respective positions of one or more objects during the computer-assisted procedure in an operating room, generating pose data representing the respective positions of the one or more objects in a reference space within the operating room; storing, by the OR computing system, log data with which to monitor a progress of the computer-assisted procedure; monitoring, the OR computing system, the progress of the computer-assisted procedure using the log data; determining, the OR computing system, a measure of progress responsive to the monitoring; and responsive to the measure of progress, communicating, by the OR computing system, a message identifying the measure of progress (and including at least some of the log data) to a remotely located monitoring computing system to monitor the OR computing system.

In respective aspects there is provided a monitoring computing system and method to monitor a remotely located operating room containing an OR computing system configured to perform a computer-assisted procedure relative to a patient including tracking respective positions of one or more objects during the computer-assisted procedure in which sensor data, representing the respective positions of the one or more objects, is received from sensors coupled to the one or more objects. The system is configured to and the method operates to receive from the OR computing system a message identifying a measure of progress of the computer-assisted procedure and optionally including at least some log data for the computer-assisted procedure stored by the OR computing system to initiate monitoring the OR computing system.

Some technical terms and definitions will be useful throughout this document. The art of tracking is chiefly concerned with positions and orientations. The terms "coordinate system", "coordinate frame", "reference frame", etc, refer to a standard basis in which positions and orientation may be described. The terms "pose" (position and orientation state estimate), position, relative position, spatial positioning, etc, all refer to describing the position and/or orientation of a rigid body with respect to some coordinate frame.

DESCRIPTION

Figures 1A, 1B, 1C:
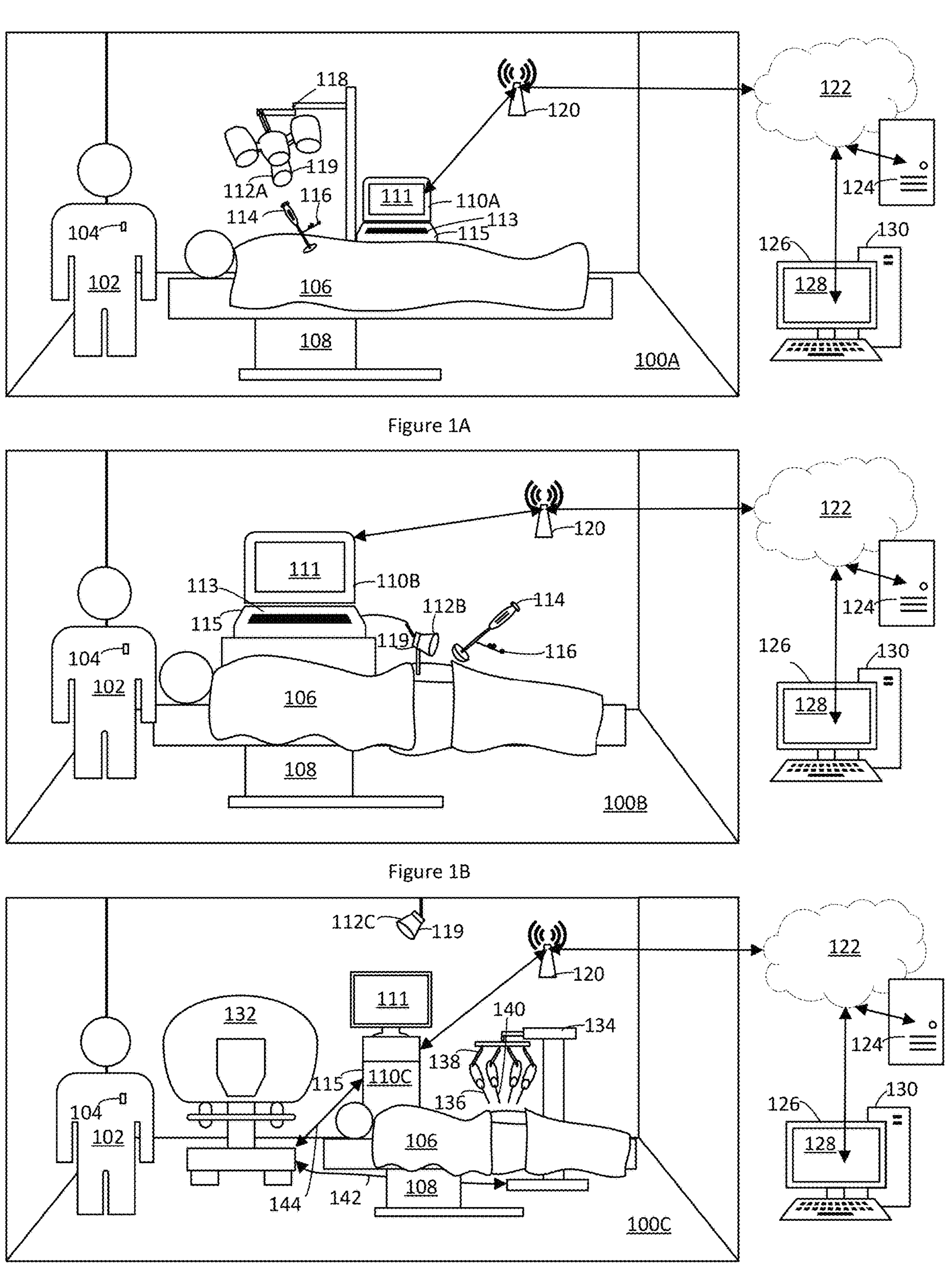
FIGS. 1A-1C show a monitored OR computing system comprising an OR computing system in an OR and a monitoring computing system external to the OR according to respective examples.

FIGS. 1A-1C show a monitored OR computing system comprising an OR computing system in an OR and a monitoring computing system external to the OR according to respective examples. FIG. 1A shows OR 100A in which a surgeon 102 or other person is attending in OR 100A. It will be appreciated that for many types of procedures that many persons including additional surgeons or other doctors (e.g. anesthesiologists), nurses, etc., may be attending (not shown) and that only some of the OR equipment is shown. Surgeon 102 is wearing a wireless microphone 104. A patient 106 is on an OR table 108. OR table 108 (or a cart (not shown)) may be configured with a suitable support for an OR computing device 110A comprising a processing unit coupled to a display device 111 and a data store 115 (e.g. memory or other storage device). Wireless microphone 104 may be coupled communicatively to OR computing device 110A. OR computing device 110A may have other input/output or I/O devices, for example a display device 111, a keyboard 113, and a pointing device (e.g. mouse), among others.

In FIG. 1A, OR computing device 110A is coupled to or is a component of a localization system for tracking objects during a computer-assisted procedure. Localization system may be optically based and comprise an OR camera 112A (a type of sensor) for tracking an object 114 such as a procedural tool as shown, a part of a patient (e.g. a bone), or any other object whose pose is desired. Object 114 has an optical tracker 116 (type of sensor) for use to indicate a pose of object 114. OR camera 112A may be mounted on a boom 118, a component of OR table 108 or a standalone unit having wheels, etc. It may be mounted to a ceiling or other surface of the OR 100A (not shown).

Optical tracker 116 may be selectively removable (for example to couple to a different object (not shown)) for the procedure. Optical tracker 116 may be passive and reflect light or active and originate light for detection and/or measurement by OR camera 112A. OR camera 112A may be a stereo camera set-up or other configuration and may provide high resolution video signals (e.g. video data) in a visible light spectrum to OR computing device 110A to visualize at least a portion of the OR 100A. OR camera 112A may provide object tracking signals (e.g. sensor data), for example tracking optical tracker 116 in an infrared (IR) spectrum or other spectrum.

OR camera 112A may have a gravity sensor 119 configured to measure gravity (e.g. accelerometers/inertial sensors) to indicate the direction of gravity relative to the object to which it is attached. Such gravity sensors 119 or optical trackers 116 may be attached to any object in the OR 100A including patient 106 to provide a reference to a patient to determine pose information (though in practice attaching to OR table 108 may be sufficient to indicate the position of the patient). It will be understood that OR camera 112A may only track optical trackers 116 when optical trackers 116 are in a field of view of OR camera 112A, which field of view is typically directed towards a treatment site relative to patient 106. Though not shown, one or more video cameras providing video data may be coupled to OR computing device 110A, for example, should OR camera 112A not provide video data and be restricted to providing sensor data.

OR computing device 110A is coupled via a communication system (e.g. a component of OR computing device 110A) to communicate to other computing devices via a network. Shown in OR 100A is a wireless access point 120 for communicating via a public communication network 122 such as the Internet. OR computing device 110A may be configured for wire based communication to other computing devices, including those external to the OR. Such other computing devices may be servers or other systems (e.g. Picture Archival and Communication Systems (PACs) storing pre-operative (pre-op) data for a patient such as patient information, reports and clinical images (e.g. Magnetic Resonance Imaging (MRI), X-Ray, or images from other modalities). Some of these servers or systems may be located geographically remote from the OR 100A or more closely such as in a same hospital (not shown).

Such other servers or systems may store configuration related data such as geometric definitions of objects to be tracked during the computer-assisted procedure and/or software (instructions) for the components. Robot kinematics applies geometry to the movement of multi-degree of freedom structures. Components of the structures (e.g. a robotic manipulator) such as the rigid bodies and joints are modeled and the models are examples of geometrical information. Robot kinematics may be used to determine relationships between the components and the position, velocity and acceleration of each of the links in the components, in order to plan and control movement and to compute actuator forces, etc. Geometric definitions for components of robots and localization systems including respective ranges of positions which the respective components may adopt in a procedure (or other constraints) may be used to define respective robot working volumes or localizer working volumes. For example, a particular robot arm having a defined shape and size (volume) may rotate through X° in a $1^{st}$ plane and Y° in a $2^{nd}$ plane to define a working volume for the arm. All of the working volumes of the robots components together may define a working volume for the robot as a whole. Geometric definitions may be constructed for respective working volumes and stored, for example, as pre-op data available to the OR computing system and/or the monitoring computing system. Geometric definitions of working volumes may comprise a volume for a structure (e.g. a link of an arm) and its range of motion constraint with which the working volume may be computed (e.g. in real-time) as needed or a pre-computed working volume.

The pose of the applicable robot or localizer component in the OR, for example a static frame or base thereof, may be made available from which pose the working volume may be represented. The working volume may be presented in a UI using a cloud of points, representative edge lines or other UI features in a virtual view of the OR. Working volumes may be defined and stored for any OR equipment, including static equipment where static here means such equipment does not have moving parts which may change the general volume of the structure.

Measurements relative to the working volumes of two or more instances of OR equipment may be made to determine how close the working volumes are in the OR and whether a risk of collision may occur (e.g. when the measurements indicate a proximity under a threshold proximity). OR equipment may include the robot or localizer as well as other equipment such as an OR table, cart, tray, tank, fixture or other equipment. Representing the working volumes of two or more components in a virtual view of the OR may illustrate the risk of collision by showing that the working volumes overlap even though the current pose adopted by one of the components is distant from the other. The working volume illustrates where the pose may be moved given the current position of the component.

Wireless access point 120 may be located externally to the OR 100A. It will be appreciated that other communication components may be used (e.g. routers, firewalls, etc.) and that the network components in FIG. 1A are simplified. OR computing device 110A may communicate with a server 124 (or more than one), which may store pre-op data for a patient, geometric definitions of objects to be tracked, etc. Server 124 may provide services to share OR data (e.g. streamed video, etc.) to monitor the OR 100A to a monitoring computing device 126, as further described and to share monitoring computing device data for assisting or intervening in a procedure via OR computing device 110A. Server 124 (or another server) and monitoring computing device 126 may define a monitoring computing system.

In practice, server 124 and monitoring computing device 126 are typically located remotely relative to OR 100A. Server 124 and monitoring computing device 126 may be located remotely relative to one another as well. While a single representative computing device (i.e. server 124) is shown with a configuration to store (and provide to others) the pre-operative data and geometric data and to provide a service to share OR data and monitoring computing device data, more than one server located in the same or different locations may be used.

Monitoring computing device 126 comprises a processing unit coupled to a display device 128 and a data store 130. As noted monitoring system 126 may be configured to monitor OR 100A, observing, assisting or intervening in a computer-assisted procedure, via OR computing device 110A, as further described.

The set-up of OR 100B in FIG. 1B is similar to OR 100A in that OR computing device 110B is similarly coupled to or is a component of a localization system. In FIG. 1B, an OR camera 112B is attached to patient 106 for the localization system. OR camera 112B may capture images (and/or video). Optical trackers 116 in the field of view of OR camera 112B are trackable by OR computing device 1101B. In the configuration of FIG. 1B, server 124 may provide services to share OR data to virtualize operating room 100B to a monitoring computing device 126, as further described and to share monitoring computing device data for assisting or intervening in a procedure via OR computing device 110B. Monitoring system 126 may be configured to monitor OR 100B, observing, assisting or intervening in a computer-assisted procedure, via OR computing device 1101B, as further described.

The set-up of OR 1000 in FIG. 1C has more differences compared to OR 100A than does OR 100B relative to OR 100A. OR 1000 is shown set-up for a robotic procedure in which there is shown a robot console 132 and a robot 134 to perform a computer-assisted procedure on patient 106. Robot 134 has a plurality of respective surgical tools/effectors (e.g. 136) positionable in space by respective motorized controllable arms (e.g. 138). A procedure site scope or camera 140 may be mounted to a one of the motorized controllable arms to provide video of the procedure. Robot console 132 is coupled to robot 134 and to OR computing device 110C via cables 142 and 144. OR computing device 110C is shown in a tower configuration common to robot procedure configurations. An OR camera 112C may be coupled to OR computing device 110C to provide wider video of the OR 110C and/or to track a position of objects in the OR, including equipment, components of any robot surgery system, personnel, etc. OR camera 112C may have a sensor to indicate a direction of gravity.

Robot console 132 may be operated by a user (e.g. 102) to position and operate the surgical tools/effectors (e.g. 136) and camera 140. Though not shown, joystick(s), finger controls, or other hand and/or foot operated input devices, etc. of robot console 132 receive inputs and generate signals to operate respective motors (not shown) and to operate the tools/effectors 136. There may be one or more motors per each of the controllable arms 138. Sensors on the arms, for example, or associated with the respective motors (e.g. one per each motor) may provide data relative to the position of the arms or motors to determine the pose of the respective tools/effectors. In some embodiments sensors may provide data relative to an angle of a segment of the arm (e.g. relative to gravity) which data may be used mathematically with geometric data for the segments, joints, etc. of the respective arm any tool attached thereto to determine a position of at least a distal end (an operating end) of the arm and, particularly the tool.

Sensor data in any of the configurations of FIGS. 1A-1C, along with the geometric definition data for respective objects (e.g. tools, etc.) can be used to compute pose data. Pose data may also be used to compute useful measurements for a procedure, for example, a relative location of two objects, such as a tool tip to a patient, a patient bone to another patient bone (e.g. femur to pelvis), etc. Pose information then is either the sensor data with which pose data may be computed or the pose data computed using the sensor data. Pose information may be sent to the monitoring computing device such as for use to present the position of the objects. In some examples a virtual view of the operating room may be presented as described herein.

In the configuration of FIG. 1C, server 124 may provide services to share OR data to virtualize operating room 1000 to a monitoring computing device 126, as further described and to share monitoring computing device data for assisting or intervening in a procedure via OR computing device 110C. Monitoring computing device 126 may be configured to monitor OR 1000, observing, assisting or intervening in a computer-assisted procedure, via the OR computing system (e.g. through OR computing device 110C), as further described.

Each of the OR computing devices 110A-110C may have similar component configurations. Each may have different programming in view of the localization system or robot system used. The OR computing device (e.g. 110A-110C) and any localization or robot system with which it is coupled in the OR (100A-100C) are examples of respective OR computing systems configured for surgical navigation. Each OR computing system comprises one or more computing units to perform a computer-assisted procedure relative to a patient. Each tracks respective positions of one or more objects during the procedure in the operating room. Sensor data, representing the respective positions of the one or more objects, is received from sensors associated with the one or more objects. Typically the association is provided by coupling a one of the respective sensors to the object. Some additional sensors and or data may be used.

During the computer-assisted procedure, each OR computing system may be configured to communicate pose information (e.g. in real time) to a monitoring computing system and ultimately to monitoring computing device 126, remotely located, for monitoring the operating room. Monitoring computing device 126 may be configured to receive the pose information and present in a graphical user interface (GUI) the respective positions of the one or more objects. The pose information may be the sensor data which can be used to calculate a pose of an object. The pose information may be pose data representing the pose of the object as calculated by the OR computing device using the sensor data.

Localization systems and surgical navigation techniques are disclosed in applicant's various patents and applications including, U.S. Pat. No. 9,138,319 B2 of Fanson et al., entitled "Method and system for aligning a prosthesis during surgery" granted Sep. 22, 2015; U.S. Pat. No. 9,247,998 B2 of Hladio et al., entitled "System and method for intra-operative leg position measurement" and granted Feb. 2, 2016; U.S. Pat. No. 9,713,506 B2 of Fanson et al., entitled "Systems, methods and devices for image registration and surgical localization" and granted Jul. 25, 2017; and US20170119475 A1 of McCabe et al., entitled "Systems, methods and devices for calculating hip center of rotation, adjusting parameters of joint replacement for pelvic tilt and calculating leg length and offset" and published May 4, 2017; each of which is hereby incorporated herein by reference.

In order to provide surgical navigation with respect to the anatomy of the patient in a computer-assisted procedure, the spatial coordinates of the anatomy of the patient (by way of example only, a pelvis in a Total Hip Arthroplasty (THA)) with respect to the OR computing system are required. This step is referred to as "registration" in this specification. Further, if image-guided surgical navigation is to be provided with respect to one or more medical images of the anatomy of the patient (which is optional), then the spatial coordinates of the anatomy of the patient are correlated to the spatial coordinates of the anatomy as it appears on one or more medical images. This step is referred to as "image registration" in this specification. Anatomical registration pertains to generating a digital positional or coordinate mapping between the anatomy of interest and the OR computing system. Similarly, image registration generates a digital positional or coordinate mapping between the anatomy of interest and one or medical images that were captured during a pre-operative scan of the anatomy. There are multiple methods to obtain this registration mapping or the registration coordinate frame between the anatomy and the OR computing system, There are also multiple methods to obtain the registration mapping or image registration coordinate frame between the anatomy and one or more medical images. It is desirable that these methods of registration are fast, so as to not increase the duration of the surgical workflow, and sufficiently accurate. The OR computing system can utilize the registration coordinate frame or the image registration coordinate frame to intra-operatively provide clinically relevant measurements to the surgeon using the system.

By way of example, FIG. 1B illustrates an OR computing system used in THA where a sensor (OR camera 112B) is attached an anatomy of a patient 106 (e.g. at the pelvis) and communicates with OR computing device 110. The pose (position and orientation) of an optical tracker 116 can be detected by the OR camera 112B and displayed on a GUI of a display device 111. Optical tracker 116 may be attached to an instrument (e.g. object 114) or to another part of the anatomy of the patient 106 (e.g. to a femur). Surgical measurements for a THA may include one or more of the following—leg length, offset, anteversion, inclination etc.

Medical image data comprises one or more raw medical images from a pre-operative scan or one or more digitally processed medical images by creating 3D surface models of anatomy represented by 3D point clouds or by using techniques of image segmentation, etc. The medical image data may be displayed in the GUI of display device 111. Construction of an image registration coordinate frame allows the surgical measurements to be displayed with respect to the medical image data.

The medical images may be used in the original format (e.g., Digital Imaging and Communications in Medicine (DICOM) files) or may be pre-processed using image segmentation and other known methods of processing medical images to create medical image data that can be used for image-guided surgical navigation. The medical images may also have been obtained with the patient standing upright, lying supine or perhaps at an orientation to the imaging equipment. If the orientation of the images with respect to an arbitrary plane is provided, the workstation of the OR computing system can, along with other inputs, utilize this orientation information during image registration in the construction of the image registration coordinate frame.

Medical images are processed to create the medical image data and to have image properties that define a direction of an identifiable anatomical axis and a location of an identifiable anatomical point of the anatomy of the patient shown in the images. For example, the identifiable anatomical axis of the anatomy may be an axis extending along the superior-inferior direction of the anatomy or may be calculated by identifying two points that lie along the identifiable anatomical axis of the anatomy, and the identifiable anatomical point may be an anterior superior iliac spine (ASIS) on a pelvis of the patient, a center of rotation of a hip joint, etc. These image properties may be defined by the imaging equipment during the capture of the medical images by placing markers on the anatomy that appear on the medical images or may be identified by user input to a computing unit or other means while post-processing the medical images to create the medical image data. Intraoperatively, a corresponding axis and a corresponding anatomical point of the patient's anatomy may be measured and determined by an intra-operative computing unit to construct the image registration coordinate frame.

The orientation of the arbitrary plane is also used to construct the registration coordinate frame and the image registration coordinate frame and it can be measured with respect to a reference element (described below) with the use of mechanical registration devices also described below. Pelvic registration, particularly useful in THA, is selected as an exemplary example: however, this description is intended to be interpreted as applicable to general anatomy and in various other surgeries. Often an optical sensor (e.g. OR camera 112B) is attached to a bone of the anatomy of the patient 106 or a steady surface such as an OR table 108. Optical tracker 116, detectable by camera 112B in up to six degrees of freedom, is located on an object being tracked, such as another bone of the anatomy of the patient, a tool, a prosthesis, etc. However, in general, the locations of camera 1128 and optical tracker 116 can be reversed without compromising functionality (e.g. fixing the target on the bone or a steady surface and attaching the sensor to the object to be tracked).

Furthermore, one skilled in the art will appreciate that the techniques, components, and methods described herein may be implemented using different tracking modalities. For example, use of traditional stereoscopic localization cameras (e.g. the Polars™ product from Northern Digital Inc. in Waterloo, ON), electromagnetic tracking systems (e.g. the Aurora™ product from Northern Digital Inc), ultrasonic localizers (e.g. see U.S. Pat. No. 8,000,926), mechanical localization devices, radio frequency (RF) localizers, etc. are contemplated.

When the camera 1128 is attached to the patient's anatomy, the reference element may be the camera 1128 itself. All measurements calculated by the OR computing system may be and preferably are with respect to the camera 112B. When the camera 1128 is attached to an OR table, a stand in the OR 110B or any other rigid location that is not on the patient, a reference element may be attached to the anatomy to allow the system to calculate the registration coordinate frame and other measurements with respect to the reference element. Optionally and without necessity, when the sensor is attached to the patient's anatomy a separate reference element may also be attached. It may be identical to the optical tracker to be detectable by the camera 112B in up to six degrees of freedom or it may have a different spatial configuration of reflective elements that allow it to be tracked by the camera 112B. The reference element provides an alternate method of use of the OR computing system that allows the camera 1128 to be positioned at a distance away from the anatomy of the patient (such as in FIG. 1A, while the reference element is attached to the patient and is within a field of view of the camera 1128 Various registration methods are taught in applicant's patents and applications including U.S. Pat. Nos. 9,713,506B2, 9,247,998 and 9,138,319B2 among others.

Figures 3A, 3B:
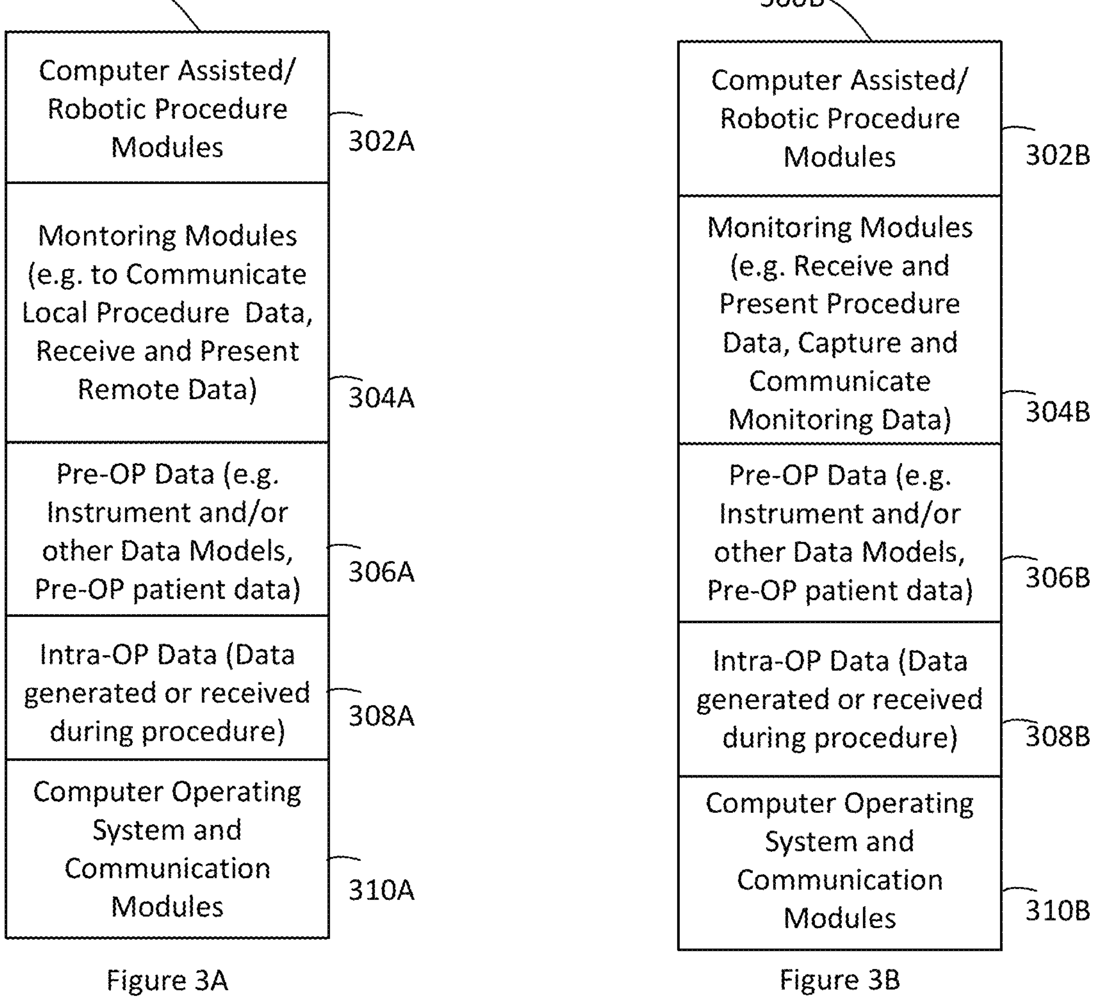
FIGS. 3A and 3B illustrate one or more data store components of an OR computing system (FIG. 3A) and a monitoring computing system (FIG. 3B) showing instructions and/or data stored respectively in accordance with an example, where such systems are as depicted in FIGS. 1A-1C.

In the monitored OR computing systems depicted in FIGS. 1A-1C, there are notionally two "sides", namely, the OR side having the OR computing system being monitored (e.g. comprising an OR computing device and a localization system or robot surgery system) and the monitoring side having the remotely located monitoring computing system (e.g. comprising a monitoring computer device and (optionally) a server). FIGS. 3A and 3B illustrate respective data store components 300A and 300B for each side, showing instructions and/or data stored respectively in accordance with an example of an OR computing system and a monitoring computing system where such systems are depicted in FIGS. 1A-1C. Each of the data store components 300A and 300B may be physically embodied in one or more physical devices (e.g. memory or other storage devices and may include databases) of the respective systems.

Figure 2:
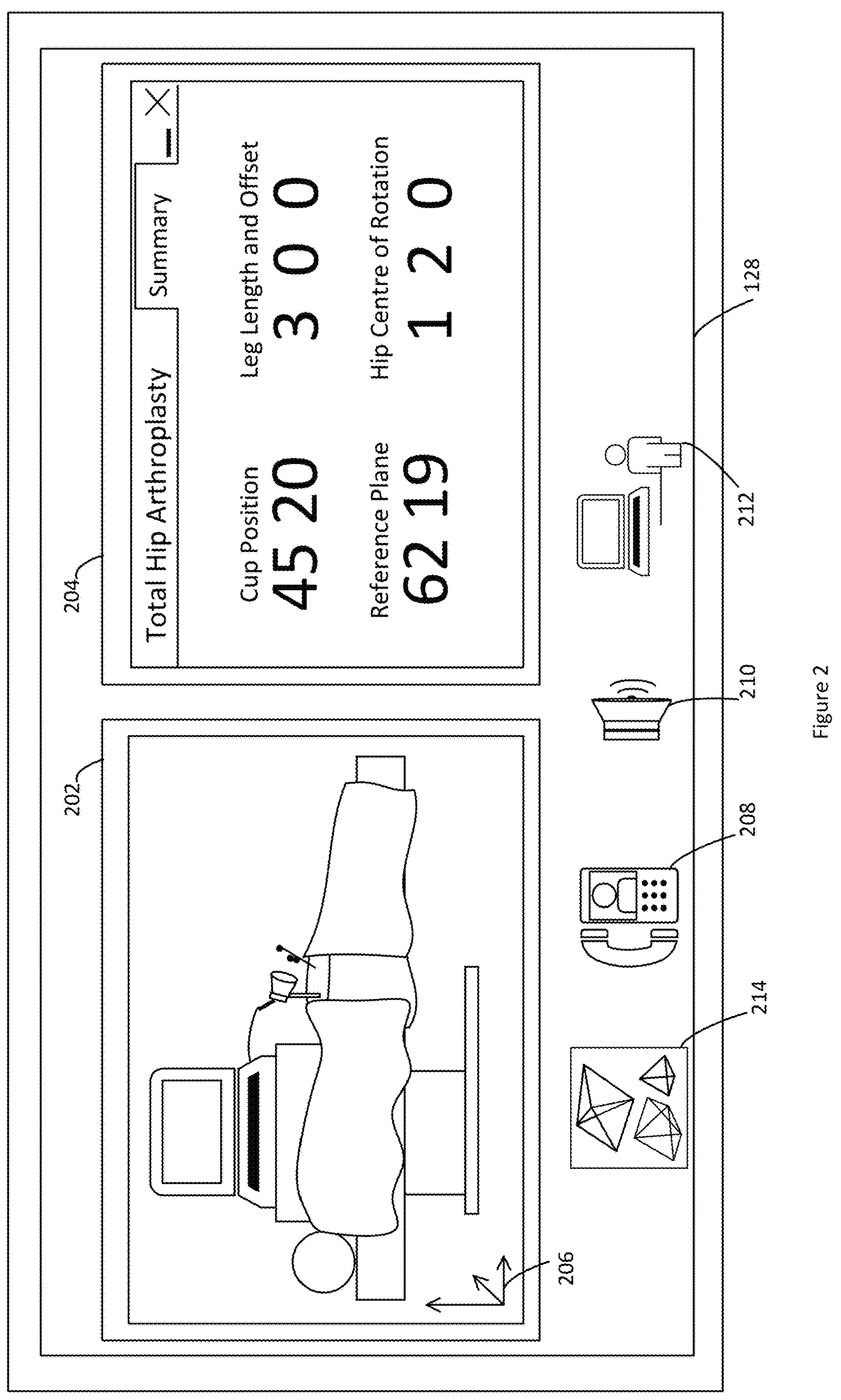
FIG. 2 is a representative screenshot of a monitoring computer system showing a virtualized view of an OR and a UI screen of an OR computing system.

FIG. 2 is a representative screenshot 200 of a monitoring computer system (e.g. display 128) showing interface elements 202 and 204 comprising, respectively, a) a virtualized view of an OR (e.g. OR 100B) and b) a UI screen of an OR computing system. It will be appreciated that monitoring computer system may be configured to present one or both such interface elements 202 and 204, among others, using data received from the OR computing system. Not shown for example is an interface element comprising a video stream from the OR. The virtualized view of an OR in the present example is a 3D rendering of at least some of the components of the OR computing system and other OR equipment in the OR. These components may be tracked or otherwise have their respective poses determined using a localization system, for example. The components may have trackers (e.g. optical trackers) such that pose information may be provided. A direction of gravity determined from a sensor associated with an optical sensor (e.g. OR camera) of the localization system. This data may be used to display the relative positions of the components responsive to the direction of gravity, for example, so that the virtual view of the components appears true (e.g. relative to a floor) as would appear to a user in the room.

Screenshot 200 further shows various controls 206, 208, 210 and 212. Control 206 is a pan/tilt/zoom control relative to interface element 202 to permit the virtualization of the OR to be presented from different points of view and notional focal length (e.g. a digital zoom). Control 208 is a video control whereby video data may be exchanged between the OR computing system and the monitoring computing system. Other options for a video control may include a control to initiate, terminate or change settings for one way video streaming to receive video data (which may include audio) from the OR. Such a control may include an ability to control (e.g. relocate) the field of view (e.g. pan/tilt) and focal length (e.g. an optical or digital zoom) of the camera. Control 210 is an audio control, for example, to engage audio from the OR such as from wireless microphone 104. Control 210 may turn audio on or off and set volume or other settings.

Control 212 is an intervention control, which may initiate intervention relative to OR computer system via the monitoring computing system. One manner of initiating intervention includes sending a message to OR computing system to request permission to intervene. Control 214 is a control for turning on or off the working volume display feature relative to interface element 202. When control 214 is on the OR virtual view in interface element 202 shows the working volume of one or more components of the OR equipment. Control 214 may provide options to select how the working volume is illustrated, whether particular components may have their respective working volume displayed or not, and how collisions are determined and represented (or not). Monitoring computing system may be configured with software modules for example to present these interface elements, controls and the associated features described.

FIG. 3A shows data store component 300A storing computer-assisted procedure modules 302A, monitoring modules 304A, pre-op data 306A, intra-operation data 308A and computer operating system and communication modules 310A. Other modules may be stored and data store component 300A is simplified.

Computer-assisted procedure modules 302A store instructions for performing an assisted procedure, for example, to track objects. Computer-assisted procedure modules 302A may include instructions to position an object using a robot, such as in response to input from a user of a robot console. In some examples procedures are performed using workflow provided by the computer-assisted procedure modules 302A. Such workflow (and hence the computer-assisted procedure modules 302A) may include GUI screens to present information via a display device (e.g. 111 or other device (e.g. which may be a part of robot console 132)). The information presented may include pre-op data and/or data generated during the procedure. Data generated may include pose information, other sensor information or measurements made from pose information or other sensor information, etc.

Monitoring modules 304A provide instructions to communicate data generated or otherwise associated with a computer-assisted procedure to the monitoring computing system (e.g. 124 and 126) and receive and process remote data received from a monitoring computing system. Monitoring modules 304A may include instructions to perform self-monitoring to trigger a message to the monitoring computing system as described further.

Pre-op data 306A may comprise pre-op patient data which may include patient information and patient images according to one or more modalities. Pre-op data 306A may include geometric definitions for objects being tracked and/or positioned in the OR, for other surgical navigation components or other OR equipment. Geometric data may be used to determine pose information, make measurements or other calculations (e.g. where two objects and/or components may collide/overlap in space) and/or to render the objects, such as in an augmented view of patient anatomy on live video or on pre-op images. In some examples, the geometric data may be 3D data models such as for rendering 3D views. In some examples, OR views may be manipulated such as by pan/tilt/zoom, etc. Pre-op data 306A may be retrieved from another computing device (e.g. a server such a server 124 or another server) for the OR computing system. In some examples the monitoring modules 304A may communicate pre-op patient data to the monitoring system.

Intra-operative data 308A comprises data generated while performing a computer-assisted procedure and/or self-monitoring of such a procedure. This is local data, relative to the OR computing system. Such data may include an identification of the OR computing system, the computer-assisted procedure being performed, anatomical registration data, patient positional reference data (i.e., relative to the registration), pose information (e.g. sensor data or pose data determined from the sensor data), direction of gravity data, measurement data determined using any intra-operative data 308A and/or pre-op data 306A, etc. In some examples workflow state (e.g. the progression through screens of computer-assisted procedure modules 302A) may be stored for providing to the monitoring computing system so that the monitoring computing device 126 may display the workflow state (e.g. at least a current screen in the GUIs associated with the workflow). The monitoring computing system is configured to generate user interface (UI) screens (e.g. stores their definitions as does the OR computing system) using the workflow state to identify a current screen to display, for example. And, using intra-operative data 308A and any pre-op data, as may be necessary, sent by the OR computing system, the monitoring computing system can populate the UI screens with the same information as is presented by the OR computing system. The intra-operative data communicated may be the actual information that is to be presented or may be data from which such information may be computed.

Intra-operative data 308A may also include monitoring data received from a monitoring computing system (i.e. remote data) for processing during the procedure, for example, audio or video data, such as from a user of monitoring computing device 126 or intervention data from monitoring device 126 to command or control components of the OR computing system. Intervention data may include interface input data such a keyboard, pointing device, screen interaction, hand and/or foot control inputs or other interface input data captured from input devices on the monitoring computing device 126 that is communicated to the OR computing system for enabling remote operation. In other instances intervention data may be output data generated from such input data received by the monitoring computing device for example using computer-assisted procedure modules 302A to perform the computer-assisted procedure, the output data communicated to the OR computing system for output thereby.

Computer operating system and communication modules 310A include instructions to provide an environment to execute the other modules as well as lower lever modules for communicating data, etc. While bright line distinctions are shown, features or functions of some modules may be performed by or shared by other modules.

FIG. 3B shows data store component 300B storing computer-assisted procedure modules 302B, monitoring modules 304B, pre-op data 306B, intra-operation data 308B and computer operating system and communication modules 310B. Other modules may be stored and data store component 300B is simplified.

On the monitoring side, in some examples the monitoring computing system may be a passive monitor, receiving data from the OR computing system for presenting via the monitoring computing device 126 but such a system may have no ability to intervene to remotely command or control the OR computing system. In such an example computer-assisted procedure modules 302B may be limited in its instructions relative to performing an assisted procedure. These modules may have operations to receive intra-operative data 308A and store it as intra-operative data 308B. The intra-operative data 308B may include pose information such as to use to present the pose of an object in a GUI and/or to perform some measurements, for example. Where the pose information is not pose data per se but raw sensor data, these computer-assisted procedure modules 302B may be configured to calculate pose data, for example, using geometric data for the respective objects (e.g. pre-op data 306B), and any anatomical registration data, direction of gravity, (from intra-operative data 308A received and stored as 308B), etc. as may be necessary. The pose data may be useful to present a view of the objects and perform certain measurements. Monitoring modules 304B may be configured to present displays such as a virtualization (virtual view) of the OR showing the layout or set-up of the OR including the pose of objects. Workflow data comprising state information may also be received to enable the monitoring system to present GUI screens as seen on the OR computing system. In this manner, the monitoring computing system may present a view of the OR and construct a view of the OR computing system GUI without having to receive a mirror of GUIs, etc., reducing communication bandwidth. However, the monitoring computing system in such an example is not configured to intervene. The virtual view may be supplemented with or otherwise presented to include a representation of working volume. When pose information for respective instances of OR equipment is available, geometric data representing respective working volumes may be obtained (e.g. from pre-op data) and, responsive to the pose information, rendered in the space representing the OR. The space representing the OR has a common reference frame for each instance of OR equipment to be rendered. The reference frame may be oriented on the display device with the assistance of the direction of gravity (i.e. intra-operative data) received from the OR computing system. Collisions between working volumes may be indicated such as by making measurements, determining distances between working volumes in the reference frame. Collisions may not only include instances where working volumes overlap but where space between working volumes is less than a threshold. Some equipment may need more "free space" than others. On a display, different working volumes may be represented using different colours (e.g. different coloured point clouds). When two different coloured point clouds overlap on the display, a third colour is presented.

In other examples, the monitoring computing system of the monitoring side may intervene and thus may require more instructions, similar to 302A to enable the monitoring computing device 126 to perform at least some aspects (e.g. computer operations) of the computer-assisted procedure. A system that can intervene may have the same monitoring abilities as a monitoring only system and be configured to receive the intra-operative data 308A and store same as intra-operative data 308B, to compute pose data from sensor data, etc., to compute measurements and present displays, including a virtualization of the OR, for example showing the layout or set-up of the OR. In contrast, monitoring modules 304B may receive (e.g. capture) input at monitoring computing device 126 and send intervention data which may be the inputs or another form (e.g. in the form of command messages, etc.) to the OR computing system.

In any of the examples, monitoring modules 304B may capture audio and/or video data and transmit same as monitoring data to the OR computing system and/or or receive audio and/or video data from the OR computing system to establish a voice and/or voice and video communication link, preferably two way, such as between users of the respective systems.

In any of the examples, the monitoring modules 304B may have instructions to present UI screens of a monitoring application and/or function including controls therefore (but not for initiating intervention in the examples where no intervention capability is provided), such as previously described with reference to FIG. 2. An intervention control could be present but invoke a message indicating the function is not available.

Monitoring modules 304B may include instructions to receive a message from the OR computing system triggered in response to self-monitoring as described further herein below.

Pre-op data 306B may comprise pre-op patient data which may include patient information and patient images according to one or more modalities. Pre-op data 306B may include geometric definitions for objects being tracked or positioned in the OR, for other surgical navigation components or other OR equipment. This data may be used to determine pose information, make measurements or other calculations (e.g.

where two objects and/or components may collide) and/or to render the objects in GUI, such as in a virtual view of the OR or on an augmented view of patient anatomy on live video or on pre-op images. In some examples, the data may be 3D data models such as for rendering 3D views. As described, in some examples, OR views may be manipulated such as by pan/tilt/zoom, etc. Pre-op data 306B may be retrieved from another computing device (e.g. a server such as server 124 or another server). In some examples, pre-op patient data may be received from the OR computing system.

Intra-operative data 308B comprises data generated during the procedure by the monitoring side. This is local data, relative to the monitoring computing system. It may also include data received from the OR computing system (i.e. remote data) during the procedure, for example, pose information, anatomical registration data and patient reference data, direction of gravity, etc. audio or video data such as from a user 102 of the OR computing system or in the OR.

Computer operating system and communication modules 310B include instructions to provide an environment to execute the other modules as well as lower lever modules for communicating data, etc. While bright line distinctions are shown, features or functions of some modules may be performed by or shared by other modules.

Figure 4A:
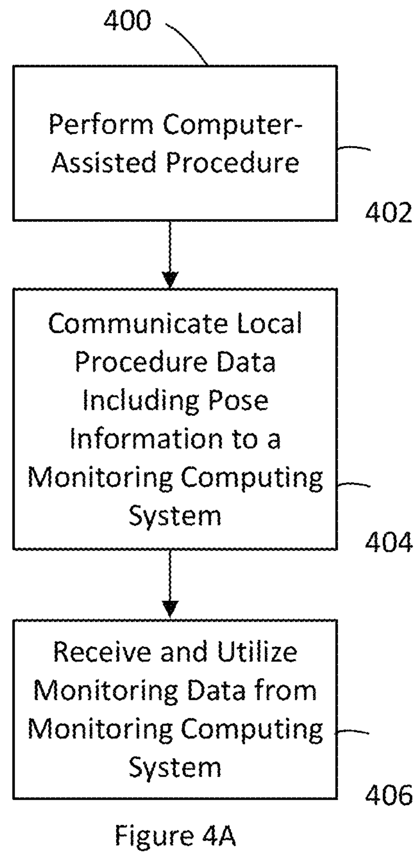
FIGS. 4A-4C, 5A, 5B, 6 and 7 illustrate example operations of the OR computing system (FIGS. 4A-4C and 6) and the monitoring computing system (FIGS. 5A, 5B and 7) shown in accordance with respective examples.

FIG. 4A is a flowchart of operations of an OR computing system, which may comprise an OR computing device communicatively coupled to a localization system and/or robot surgery system. At least some of these components, alone or together, comprises at least one processing unit coupled to a data store comprising a memory or other storage and a communication system. The communication system is configured to couple the OR computing system to a communication network. The data store stores instructions which, when executed by the at least one processing unit, configure operations (e.g. 400) of the OR computing system. Operations 400 include, at 402, performing a computer-assisted procedure relative to a patient, tracking respective positions of one or more objects during the procedure in an operating room in which sensor data, representing the respective positions of the one or more objects within the operating room, is received from sensors associated with the one or more objects. At 404 operations include, during the computer-assisted procedure (e.g. in real time), communicating intra-operative data generated during the procedure, including pose information to a remotely located monitoring computing system for monitoring the operating room, the monitoring computing system configured to receive the intra-operative data (including pose information) and present the intra-operative data comprising the respective positions of the one or more objects.

The pose information may comprise one or both of: sensor data with which to calculate a pose of an object; and pose data representing the pose of the object as calculated by the OR computing device using the sensor data.

At 406, operations include receiving and utilizing monitoring data generated by the monitoring computing system. The monitoring data may be selected from audio data, video data and intervention data, for example to control the OR computing system.

In order to associate the pose of the objects with that of the patient, the pose information may include pose information of a patient reference for the patient. A patient reference may be a camera coupled to the patient or an optical tracker associated to the patient. Pose information for a patient reference may be determined once and sent once if the patient does not move during a procedure.

During the performance of the computer-assisted procedure, typically toward the start thereof, the instructions configure the OR computing system to register the patient to the OR computing system to define anatomical registration data, a type of intra-operative data; and communicate the anatomical registration data to the monitoring computing system to enable the monitoring computing system to present the position of the patient and/or the respective positions of the one or more objects relative to the position of the patient.

The computer-assisted procedure may comprise one of: performing a computer-assisted localization to track the one or more objects; and controlling a positioning of at least one of the one or more objects using a robot. When a computer-assisted localization is performed, the sensors may be components of an optical localization system at least one of which sensors is attached to the one or more objects. When the computer-assisted procedure comprises controlling the positioning of at least one of the one or more objects using the robot, the sensors are coupled to the robot.

The intra-operative data may comprise any of: pose information of a robotic manipulator; measured forces of a robotic end effector; measured speed or revolutions per minute (RPM) of a robotic end effector; pose information from an optical sensor; pose information of a medical imaging device (such as a C-arm); and timestamp data.

In some examples, one of the sensors comprises a localization camera and the sensor data includes a raw video feed of the localization camera. At least one of the one or more objects are selected from procedural tools and a part (bone) of the patient.

Though not shown, the OR computing system may communicate pre-operative data for the patient to the monitoring computing system for use to present during the monitoring.

The OR computing system may comprise at least one of a video camera and a microphone to capture OR video and/or voice data during the procedure and the OR computing system may communicate the OR video and/or voice data to the monitoring computing system.

When performing the procedure, the OR computing system may be configured to perform the computer-assisted procedure using workflow comprising UI screens. In some examples, the OR computing system may be configured to a) maintain a workflow state representing progress in the workflow; and communicate the workflow state to the monitoring computing system; and, in some examples, b) mirror a display device of the OR computing device, sending an image thereof to share the UI screens (e.g. in accordance with a progress of the workflow) to the monitoring computing system. This sharing of state or actual UI screens enables the monitoring computing device to present the UI screens of the workflow in association with a virtual view of the operating room, showing the location (including the pose if such information is received) of components of the OR computing system or other OR equipment. As noted, mirroring screens by sending an image may not be preferred for bandwidth purposes.

Figure 4B:
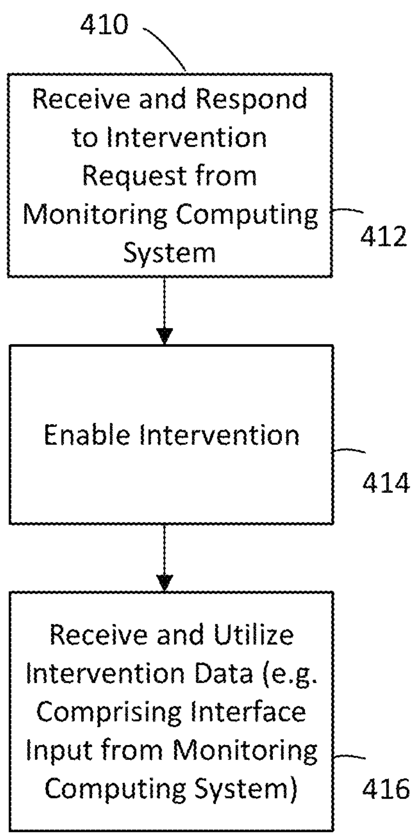

It may be that in some examples, the OR computing system may only permit intervention in response to a request (e.g. switching from a monitoring only state to an intervention state with monitoring). As shown in FIG. 4B operations 410 provide for a switching to a monitoring state. At 412, operations receive and respond to an intervention request. At 414 operations enable intervention. In some examples, this may simply entail permissioning to receive additional message types (e.g. intervention data) from the monitoring computing system. In some it may invoke a mirroring of screens to the monitoring computing system to see exactly what is shown on the OR computing system to begin mirroring the UI screen(s) to the monitoring computing system. At 416, intervention data is received and utilized. Intervention data may be interface input such as previously described which is used as if received directly from input devices of the OR computing system.

Intervention may include navigating the workflow (UI screens) of the procedure, inputting data, invoking features or functions including those of other applications and/or the operating system, etc. In some examples, it may include providing credentials (e.g. user name and password) to invoke protected features only accessible to administrators or other qualified users in accordance with a policy (rules) of the computer-assisted procedure application or the operating system.

In some examples, an OR camera (e.g. 112C) or other camera (not shown) providing video data to the monitoring computing system, may be controllable to pan, tilt and/or zoom to relocate its field of view, etc. A position of such a camera may be controlled by the OR computing device (e.g. 110C) such as via an interface such as a UI screen or an API. The monitoring computing system may be configured to send intervention data, whether as input to the UI or API, to relocate the position of the camera.

Figure 4C:
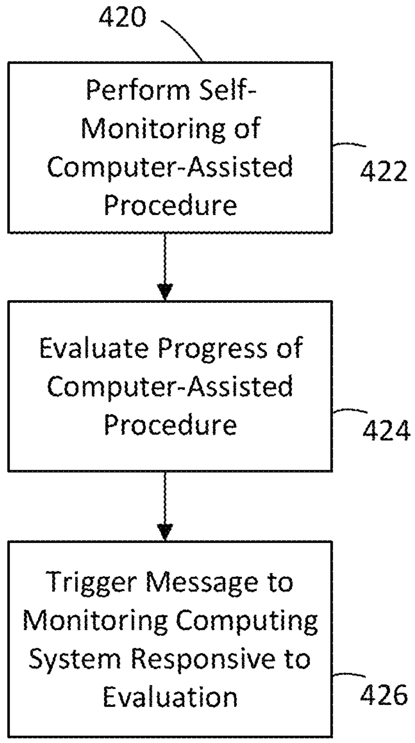

As shown in FIG. 4C, the OR computing system may perform self-monitoring operations 420 and request a monitoring by a monitoring system. At 422 the OR computing system performs self-monitoring of the progress. Self-monitoring may include logging data and evaluating such data as described further. At 324 operations determine an evaluation of the progress. And at 426, responsive to the evaluation, operations communicate a message to the monitoring computing system, for example, to initiate a monitoring of the OR computing system. In accordance with an example, a self-monitoring operations are detailed in FIG. 6 described herein below.

Figure 5A:
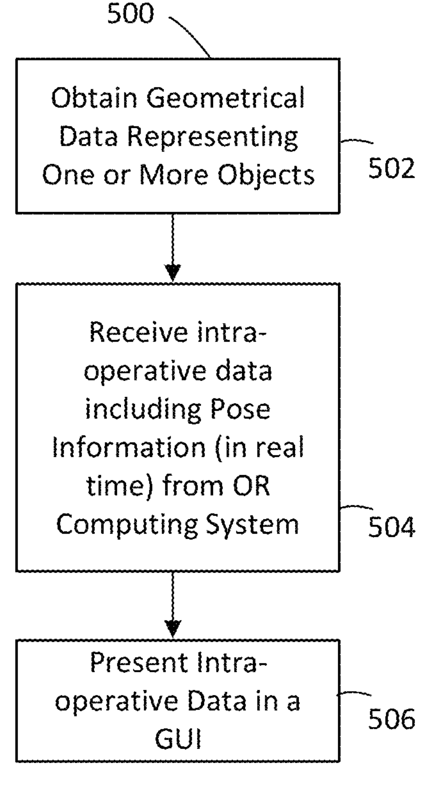

FIG. 5A is a flowchart of operations 500 of a monitoring computing system to monitor a remotely located operating room containing an OR computing system. The OR computing system is configured to perform a computer-assisted procedure relative to a patient, tracking respective positions of one or more objects during the computer-assisted procedure in which sensor data, representing the respective positions of the one or more objects, is received from sensors coupled to the one or more objects. The monitoring computing system comprises at least one processing unit coupled to a data store comprising a memory or other storage and further coupled to a display device and a communication system to communicate with the OR computing system via a network. The data store stores instructions which, when executed by the at least one processing unit, configure the monitoring computing system to perform operations 500.

Operations 500 include, at 502, obtaining geometrical data representing the one or more objects. Operations include, at 504 receiving intra-operative data including pose information (in real time) from the OR computing system. At 506 operations include presenting in a GUI, such as by displaying on the display device, respective positions of the one or more objects using the pose information and the geometrical data. The pose information may comprise one or both of sensor data with which to calculate a pose of an object and pose data representing the pose of the object as calculated by the OR computing device using the sensor data.

The pose information may include a patient reference (pose information) of a patient and the monitoring computing system may be configured to: receive anatomical registration data (a type of intra-operative data) determined from a patient registration of the patient in the OR computing system; and use the anatomical registration data and patient reference to present in the GUI at least one of a position of the patient and the respective positions of the one or more objects relative to the position of the patient.

The sensor data may comprise one or both of: camera measurements from a camera sensor of an optical localization system; and pose data calculated using the camera measurements. In some examples, at least one of the sensors sense motor encoder measurements of motors of a robot controlling the positioning of at least one of the one or more objects. In such a case the sensor data may comprises one or both of: the motor encoder measurements; and pose data calculated using the motor encoder measurements.

The one or more objects may be selected from procedural tools and a part (e.g. bone) of the patient. In some examples, the monitoring computing system is configured to receive pre-operative data for the patient to determine the GUI.

In some example, the monitoring computing system may comprising at least one a video camera and a microphone to capture monitoring video and/or voice data and the monitoring computing system may be configured to communicate the monitoring video and/or voice data to the OR computing system.

The computer-assisted procedure may be performed using Workflow with UI screens. A workflow state may be monitored by the OR computing system and such state transmitted (e.g. as in intra-operative data) in some examples. In some examples, the UI screen(s) of the OR computing system may be mirrored (sending images) to the monitoring computing system. In some examples workflow state may be sent and received such as during a monitoring only state and mirroring data received (which may supplement or replace workflow state generated screens on the monitoring computing system) such as during an intervention state. Thus the monitoring computing system may be configured to receive state data only or mirroring data only or both types and present the UI screens of the workflow.

Figure 5B:
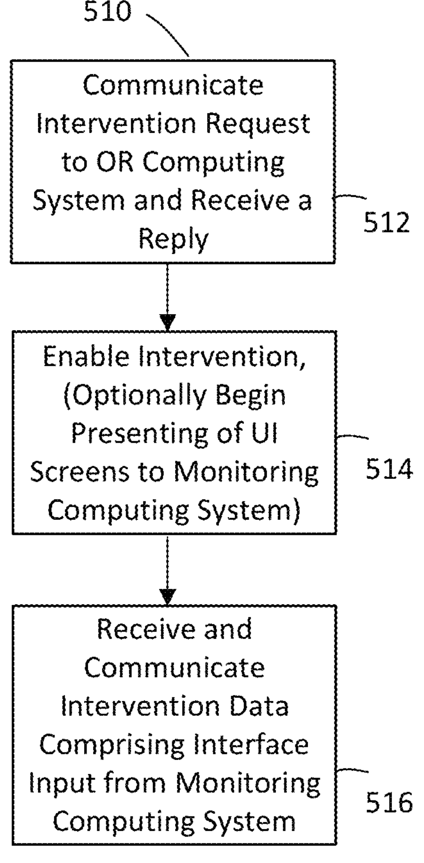

As shown in FIG. 5B, the monitoring computing system may be configured with operations 510 to request an intervention relative to the OR computing system to control at least one of its operations. At 512 operations communicate an intervention request to the OR computing system and receive a reply. At 514 operations, intervention is enabled. In some examples, for example, in a separate window of the display device (e.g. display device 128), screens of the OR computing system may be mirrored (e.g. images received from the OR computing system). At 516, interface input is received by the monitoring computing system and communicated to the OR computing system. The interface input may be relative to the screens of OR computing system mirrored or generated using workflow state (received from the OR computing system) on the monitoring computing system so that the monitoring computing system may effectively control at least one operation of the OR computing system. A representative operation which may be controlled, at least in part by the monitoring computing system, is a transition within the workflow, for example from one UI screen to a next UI screen. While the OR computing system receives intervention data from the monitoring computing system it may also receive (e.g. continue to receive) input data from any input devices coupled to the OR computing system (e.g. within the OR). These input devise may include a keyboard, pointing device, sensors of a localization system or robotic system, microphone, camera, etc. It is noted that the screens mirrored on the monitoring computing system may including screens generated by other applications or software of the OR computing system such as screens from an operating system, etc.

The geometrical data may comprise 3D data models (e.g. CAD, etc.) for rendering 3D objects in a user interface and the monitoring computing system may use the positional information and the respective data models to render a 3D view of at least the one or more objects in the operating room.

In some examples, the OR room may be virtualized in greater detail. The OR computing system comprises or is coupled to components of a localization system or a robotic surgery system and OR contains components defining other OR equipment. The intra-operative data incudes respective component positional information for such components and the monitoring computing system is configured to obtain geometrical data representing at least one of the respective components of the OR computing system and/or the other OR equipment to present a rendering of the at least one of the respective components in a virtual view of the OR responsive to the respective component positional information.

The virtual view showing the OR components may be enabled with UI controls to pan, tilt or zoom in/out the virtual view. The virtual view and the UI screens of the OR computing system (whether produced from workflow state or from mirrored data) and any video data may be presented in different windows or other UI constructs (e.g. overlays, pop-ups, etc.) in display device 128. In this manner a user of the monitoring computing system may better visualize what is seen by a user in the OR. It will be understood that video views may only show portions of the OR and that a 3D virtual view may permit a better understanding of the OR, the object (and patient) therein.

The monitoring computing system may determine positional state information for the one or more objects using the geometrical data and the pose information. Positional state information may include position, speed, acceleration, pressure/force, proximity and other measures.

Figures 6, 7:
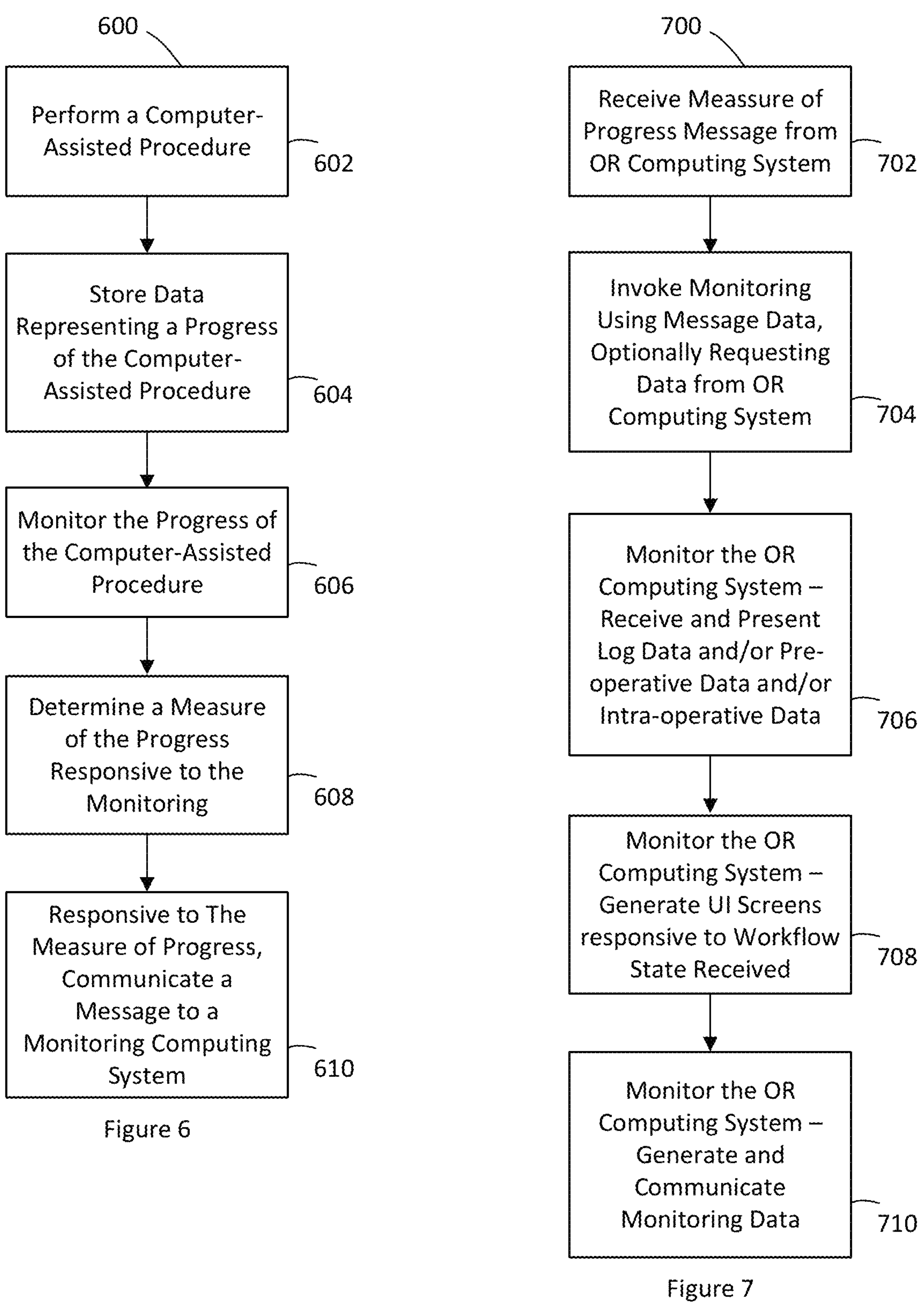

FIG. 6 is a flowchart of operations 600 of an OR computing system, for example, such as described with reference to FIGS. 4A-4C. Operations 600 detail a self-monitoring feature. At 602, the OR computing system performs a computer-assisted procedure, for example, tracking respective positions of one or more objects during the computer-assisted procedure in an operating room, generating pose data representing the respective positions of the one or more objects in a reference space within the operating room. At 604, log data is stored representing a progress of the computer-assisted procedure. Log data herein is a generic term representing any intra-operative data generated during the procedure, time stamp data, or data generated from any of same.

At 606, operations monitor the progress of the computer-assisted procedure. At 608 operations determine a measure of the progress responsive to the monitoring of the progress; and, at 610, responsive to the measure of progress, operations communicate a message identifying the measure of progress (and, optionally, including at least some of the log data) to the monitoring computing system. The message identifies the OR computing system as may be necessary.

The OR computing system may comprise a camera and be configured to receive images from the camera and store images as log data. The amount of image data stored may be limited such as by writing to a (circular) buffer of a defined size and overwriting same as it is filled.

The OR computing system may be configured to perform the computer-assisted procedure using workflow including UI screens, the log data stored may be workflow state data. Any log data may be associated with a time stamp to mark a time of occurrence and/or time of logging.

The measure of progress may be a failure to progress the state of the workflow from one state to a next state or a repetition of one state of the workflow. The failure may be associated with an amount of time, for example taking more than a threshold amount or repeating a state two or more times within a threshold amount of time. The measure of progress may be responsive to an expiry of a threshold period of time to progress the state of the workflow from one state to a next state. The measure of progress may be based on exceeding a threshold of the number of failed localization measurements (e.g. due to invalid or corrupted pose data).

The log data may be monitored (analyzed) using rules in a rules based manner looking for example, for failures to progress the procedure or for the recording of specific instances or co-instances of data. For example, the computer-assisted procedure may include performing certain calibrations. Calibration operations may log outcomes such as a status or calibration data results (measures or calculations using measures). The rules may analyze the log data and determine a measure of progress accordingly, determining a failure to progress that is responsive to the calibration. The OR computing system may thus store rules to analyse the log data and determine the measure of progress in response to the rules analysis.

The rules may determine a severity indicator for the measure of progress and communicate the message responsive to the severity indicator. The severity indicator may direct how or to whom the message is sent. In one example, the measure of progress may indicate that follow-up training of personnel is indicated. In one example, the measure of progress may indicate service is necessary. The severity indicator may indicate an urgency of the service need and direct a lower level need message to be delivered via email and a higher level need message to be delivered via SMS/text. In one example, the severity indicator may indicate that an intervention is necessary. Different severity indications for a particular measure of progress may generate different messages to different recipients. These messages may be communicated in different manners such as via email, short message service (SMS), text, instant message (IM), etc. to training or services personnel or through an application programming interface (API) or other communication interface to a monitoring computing system to request monitoring and/or monitoring and intervention.

In one example, a message may be communicated to a monitoring computing system. The message may be received and presented by the monitoring computing system via an interface (e.g. UI on display device 128). In response to the message, a user of the monitoring computing system may begin monitoring the OR computing system (which may include sending a message that monitoring has commenced or may request that it be commenced). Initiating monitoring may entail receiving additional log data from the OR computing system (e.g. recently logged video, or other intra-operative data generated by the OR computing system (registration data, pose information, etc.)). A message may be sent to the OR computing system to pull this additional log data (e.g. invoke a sending). The monitoring computing system may present the intra-operative data received. For example, the monitoring computing system may show any UI screens including intra-operative data or data derived therefrom in the UI screens. In some examples, the data received may be a workflow state (e.g. Procedure THA, Probe Calibration Step, Screen 2) and sensor data (e.g. data with which a position of a probe (tool) is indicated or may be determined). The monitoring computing system may present the corresponding UI screen from a definition thereof stored at or accessible to the monitoring computing system including populating that UI screen with the position of the tool or any rendering thereof according to the UI Screen definition, etc. An audio and/or video channel may be initiated between the two systems. Intervention may be indicated and intervention data generated as described.

The OR computing system may be configured to: communicate the message during the computer-assisted procedure; receive monitoring data from a remotely located monitoring computing system during the computer-assisted procedure; and utilize the monitoring data from the monitoring computing system via the OR computing system. The monitoring data from the monitoring computing system may be audio and/or video data for presenting via an audio and/or display device and/or intervention data to at least partially control the OR computing system.

The OR computing system may be coupled to a microphone and/or video camera and communicate OR audio and/or video data from the operating room to the monitoring computing system.

The OR computing system may be configured to send (e.g. after the message is sent) additional data from at least one of the log data or intra-operative data generated by the OR computing device to the monitoring computing system. The log data or data generated comprises any of: camera image data, intra-operative data including pose data determined from the camera image data, measurement data determined from the pose data, screenshot data, workflow state data, pre-operative patient data, and timestamp data for any of the data generated during the procedure.

FIG. 7 shows operations 700 of a monitoring computing system, for example, responsive to a message from an OR computing system. The monitoring computing system may be configured as describe previously. At 702, a message is received from an OR computing system, the message generated in response to (and indicating) a measure of progress of the OR computing system as it performs a computer-assisted procedure.

Depending, for example, on the form of message, a monitoring of OR computing system may be invoked in different manners (e.g. at 704). The message may be an email and include a browser-based interface link to invoke a browser-based application or other invocation. The message may include log data and/or data identifying the OR computing system with which the monitoring computing system can initiate the monitoring and/or pre-operative data for a patient. Monitoring may request additional log data and/or intra-operative data and/or pre-operative data (also at 704). Monitoring may include receiving and presenting (at 706) such log data and/or intra-operative data and/or pre-operative data. In some examples, a virtual view may be presented of the OR in which at least some of the OR computing system is located. In some examples, UI screens of the OR computing system are presented such as may be generated from workflow state data received (at 708). Operations at 710 generate and communicate monitoring data, for example intervention data and/or audio or video data as described, for action by the OR computing system.

While the teachings here discuss monitoring in real time, exchanging data during a procedure, it is envisioned that intra-operative data may be stored (logged) for later retrieval and "playback", for example, to reproduce the procedure. The stored intra-operative data may include raw sensor data and/or registration data, workflow state data, etc. with time stamps or ordered in a manner to facilitate an ordered play back.

While the invocation of monitoring has been described with reference to a self-monitoring operation of the OR computing system other invocation triggers may be used. In one example, the OR computing system may automatically send a message to the monitoring computing system each time a computer-assisted procedure is commenced. The message may identify the OR computing system, the computer-assisted procedure to be performed, etc. The message may be a request to invoke a monitoring. The message may be a notification that a procedure has commenced. The notification may be presented (e.g. in a GUI) such as in a list or other representation (e.g. a map) of active procedures by OR computing system. The GUI may enable a selection of the procedure/OR computing system to invoke a monitoring. In some examples, the OR computing system may be configured with a help button or other control to invoke the sending of a message to request/invoke monitoring.

While various examples are discussed herein, unless stated otherwise or it is not logically possible, features and functions of any example may be combined and/or used with those of another example. By way of illustration, an OR computing system configured to communicate with a remotely located monitoring computing system to provide intra-operative data thereto may also be configured to perform self-monitoring.

We claim:

1. A distributed computing system to monitor a computer assisted procedure performed in an operating room (OR), the computing system comprising:

- a monitoring computing system located externally to the OR and comprising:
  - at least one first processor coupled to each of:
    - a first data store comprising a first memory or other first storage storing first instructions;
    - a first display device; and
    - a first communication system to communicate via a network with an OR computing system located within the OR; and
- the OR computing system, the OR computing system comprising:
  - at least one second processor coupled to each of:
    - a second data store comprising a second memory or other second storage storing second instructions;
    - a second display device; and
    - a second communication system to communicate via the network with the monitoring computing system; and
- wherein:
  - the second instructions are executable by the at least one second processor to configure the at least one second processor to assist an OR user to perform the computer-assisted procedure relative to a patient in the OR by:
    - tracking respective positions of one or more objects during the computer-assisted procedure using sensor data representing the respective positions of the one or more objects;
    - communicating intra-operative data including pose information for the one or more objects as tracked to the monitoring computing system via the network for passively monitoring the computer assisted procedure in the OR without intervening in the performing of the computer assisted procedure;

the first instructions are executable by the at least one first processor to configure the at least one first processor to monitor the computer assisted procedure performed by the OR user using the OR computing system by:

receiving via the network from the OR computing system the intra-operative data including pose information for the one or more objects as tracked; and present, to a user of the monitoring computing system and in a graphical user interface (GUI) via the first display device, at least some of the intra-operative data including the respective positions of the one or more objects using the pose information and geometrical data for the one or more objects for passively monitoring the computer-assisted procedure without intervening;

the pose information comprises one or both of: sensor data from sensors located in the OR and coupled directly or indirectly to the OR computing system to calculate a pose of an object; or pose data representing the pose of the object as calculated by the OR computing system using the sensor data.

2. The distributed computing system of claim 1 wherein the computer-assisted procedure comprises one of: performing a computer-assisted localization to track the one or more objects; or controlling a positioning of at least one of the one or more objects using a robot.

3. The distributed computing system of claim 1 wherein the sensor data comprises one or both of: camera measurements from a camera sensor of an optical localization system; or pose data calculated using the camera measurements.

4. The distributed computing system of claim 1 wherein the sensor data comprises a motor encoder measurement of motors of a robot controlling the positioning of at least one of the one or more objects; and wherein the pose information comprises one or both of: the motor encoder measurement; or pose data calculated using the motor encoder measurement.

5. The distributed computing system of claim 1 wherein the monitoring computing system further comprises at least one of a video camera and a microphone to capture monitoring video and/or voice data of the user of the monitoring computing system and wherein the first instructions configure the at least one first processor to communicate the monitoring video and/or voice data to the OR computing system for presenting within the OR and to receive video and/or voice data from the OR user via the OR computing system to establish a voice and/or voice and video communication link between the OR user and the user of the monitoring system to communicate to help the OR user to perform the computer-assisted procedure.

6. The distributed computing system of claim 1 wherein the first instructions are further executable to configure the at least one first processor to:

receive one of:

a) a workflow state from the OR computing system representing a progress of the OR user in a workflow comprising UI screens for the computer-assisted procedure; or b) a mirror of a display device of the OR computing system sharing the UI screens in accordance with the progress of the OR user in the workflow for the computer-assisted procedure; and present the UI screens of the workflow via the first display device to the user of the monitoring computing system to passively monitor the computer-assisted procedure.

7. The distributed computing system of claim 1 wherein the first instructions are further executable to configure the at least one first processor to:

receive input to define intervention data to take over control of the OR computing system from the OR user and communicate the intervention data to the OR computing system, wherein the input comprises user input from the user of the monitoring computing system who is distinct from the OR user located in the OR, the intervention data enabling the user of the monitoring computing system to intervene for help in the computer-assisted procedure; and receive from the OR computing system and present to user of the monitoring computing system further intra-operative data including further pose information for the one or more objects as further tracked in response to the intervention by the monitoring computing system.

8. The distributed computing system of claim 1 wherein the first instructions configure the at least one first processor to:

obtain the geometrical data comprising 3D data models for rendering 3D objects in a user interface; and use the positional information and the respective data models to render a 3D view of at least the one or more objects in the GUI.

9. The distributed computing system of claim 1 wherein the OR computing system comprises or is coupled to components of one of a localization system and a robotic surgery system and wherein the first instructions configure the monitoring computing system to access geometrical data representing at least one of the components to present a rendering of the at least one of the components in a virtual view showing a layout of OR equipment of the OR, wherein the at least one of the components are distinct from the one or more objects as tracked for the computer-assisted procedure.

10. The distributed computing system of claim 9 wherein the first instructions are executable to further configure the at least one first processor to provide a control selected from a pan control to pan the virtual view, a tilt control to tilt the virtual view, a zoom control to zoom in and/or out the virtual view, and a working volume control to display a working volume for at least one component of OR equipment in the virtual view.

11. The distributed computing system of claim 1 wherein the first instructions are executable to further configure the at least one first processor to receive a message and log data from the OR computing system to initiate monitoring by the monitoring computing system to provide help for the procedure, wherein the log data provides a representation of a progress of the computer-assisted procedure prior to the initiation of monitoring for presenting by the monitoring computing system.

12. The distributed computing system of claim 1, wherein the first instructions are executable to further configure the at least one first processor to selectively monitor a plurality of respective OR computing systems each of the plurality of OR computing systems actively performing respective computer-assisted procedures, wherein a user interface is configured to receive input to select one of the respective computer-assisted procedures or one of the plurality of OR computing systems to invoke the monitoring.

13. A computer implemented method to receive monitoring by a remotely located monitoring computing system, the method for a distributed computing system comprising an operating room (OR) computing system located in an OR and the remotely located monitoring computing system located externally to the OR, the method comprising:

by the OR computing system:

performing a computer-assisted procedure relative to a patient, tracking respective positions of one or more objects during the computer-assisted procedure in the OR in which sensor data, representing the respective positions of the one or more objects within the OR, is received by the OR computing system from sensors associated with the one or more objects; and generating intra-operative data for the procedure including pose information for the one or more objects as tracked;

presenting intra-operative data via a display device coupled to the OR computing system in the OR for at least one OR user, the at least one OR user located in the OR;

communicating the intra-operative data via an external communication network to the remotely located monitoring computing system for monitoring the OR for passively monitoring the computer assisted procedure in the OR without intervening in the performing of the computer assisted procedure;

by the remotely located monitoring computing system:

receiving and presenting, to at least one monitoring user distinct from the at least one OR user, the intra-operative data in a graphical user interface (GUI) comprising the respective positions of one or more of the objects to passively monitor the computer-assisted procedure without intervening;

wherein the pose information comprises one or both of:

the sensor data with which to calculate a pose of an object; and pose data representing the pose of the object as calculated by the OR computing system using the sensor data.

14. The method of claim 13 comprising, by the OR computing system, self-monitoring a progression of the computer-assisted procedure and, responsive to the progression, communicating a message to the monitoring computing system to invoke a remote monitoring of the OR computing system.

15. The method of claim 13 wherein the self monitoring comprises:

storing log data with which to monitor a progress of the computer-assisted procedure;

monitoring the progress of the computer-assisted procedure using the log data;

determining a measure of progress responsive to the monitoring; and responsive to the measure of progress, communicate a message identifying the measure of progress to the remotely located monitoring computing system to monitor the OR computing system.

16. The method of claim 15 wherein the measure of progress is: (i) a failure to advance the state of a workflow from one state to a next state; (ii) a repetition of one state of the workflow; or (iii) responsive to an expiry of a threshold period of time to advance the state of the workflow from one state to a next state.

17. The method of claim 15 comprising, by the OR computing system:

communicating the message during the computer-assisted procedure;

receiving monitoring data from the monitoring computing system during the computer-assisted procedure; and utilizing the monitoring data from the remotely located monitoring computing system via the OR computing system, wherein the monitoring data from the remotely located monitoring computing system is one or both of: i) intervention data to at least partially control the OR computing system; and ii) audio and/or video data to present via an audio and/or display device.

18. The method of claim 13 further comprising, by the monitoring computer system:

receiving input to define intervention data to take over control of the OR computing system from the OR user, wherein the input comprises user input from the user of the monitoring computing system, the intervention data enabling the user of the monitoring computing system to intervene for help in the computer-assisted procedure;

communicating the intervention data to the OR computing system and receiving from the OR computing system and presenting to user of the monitoring computing system further intra-operative data including further pose information for the one or more objects as further tracked in response to the intervention by the monitoring computing system.

19. The method of claim 13, wherein the OR computing system comprises or is coupled to components of one of a localization system and a robotic surgery system, and whether the method further comprises, by the monitoring computer system:

accessing geometrical data representing at least one of the components to present a rendering of the at least one of the components in a virtual view showing a layout of OR equipment of the OR, wherein the at least one of the components are distinct from the one or more objects as tracked for the computer-assisted procedure; and providing a control selected from a pan control to pan the virtual view, a tilt control to tilt the virtual view, a zoom control to zoom in and/or out the virtual view, and a working volume control to display a working volume for at least one component of OR equipment in the virtual view.

20. The method of claim 13, wherein the monitoring computer system is coupled to a plurality of OR computing systems in respective ORs, and the method further comprises, by the monitoring computer system:

selectively monitoring the plurality of respective OR computing systems, each of the plurality of OR computing systems actively performing respective computer-assisted procedures, wherein a user interface of the monitoring computer system is configured to receive input to select one of the respective computer-assisted procedures or one of the plurality of OR computing systems to invoke the monitoring.

* * * * *